(12) United States Patent
Zayfert et al.

(10) Patent No.: US 8,439,686 B2
(45) Date of Patent: May 14, 2013

(54) DEVICE, SYSTEM, AND METHOD FOR TREATING PSYCHIATRIC DISORDERS

(76) Inventors: Claudia Zayfert, White River, VT (US); James Albert Cartreine, Roxbury, MA (US)

(*) Notice: Subject to any disclaimer, the term of this patent is extended or adjusted under 35 U.S.C. 154(b) by 571 days.

(21) Appl. No.: 12/501,156

(22) Filed: Jul. 10, 2009

(65) Prior Publication Data
US 2010/0010371 A1  Jan. 14, 2010

Related U.S. Application Data

(60) Provisional application No. 61/079,648, filed on Jul. 10, 2008.

(51) Int. Cl.
*A61B 5/00* (2006.01)
*G09B 5/06* (2006.01)
*G09B 1/00* (2006.01)

(52) U.S. Cl.
USPC ............................ 434/236; 600/558; 600/559

(58) Field of Classification Search .................. 434/236; 600/558, 559
See application file for complete search history.

(56) References Cited

U.S. PATENT DOCUMENTS

| | | | | |
|---|---|---|---|---|
| 5,267,942 A * | 12/1993 | Saperston | ....................... | 600/28 |
| 5,807,114 A * | 9/1998 | Hodges et al. | ................ | 434/236 |
| 5,913,310 A | 6/1999 | Brown | | |
| 6,012,926 A * | 1/2000 | Hodges et al. | ................ | 434/236 |
| 6,057,846 A * | 5/2000 | Sever, Jr. | ........................ | 345/419 |
| 6,425,764 B1 * | 7/2002 | Lamson | ........................ | 434/236 |
| 6,896,655 B2 * | 5/2005 | Patton et al. | .................. | 600/300 |
| 7,128,577 B2 * | 10/2006 | Renaud | .......................... | 434/236 |
| 7,972,140 B2 * | 7/2011 | Renaud | .......................... | 434/236 |
| 7,983,920 B2 * | 7/2011 | Sinclair, II | .................... | 704/270 |
| 2003/0059750 A1 | 3/2003 | Bindler | | |
| 2008/0242954 A1 * | 10/2008 | Naya et al. | .................... | 600/300 |
| 2008/0287821 A1 * | 11/2008 | Jung et al. | ..................... | 600/544 |
| 2010/0010371 A1 * | 1/2010 | Zayfert et al. | ................ | 600/558 |

FOREIGN PATENT DOCUMENTS

| | | |
|---|---|---|
| WO | WO9722324 A1 | 6/1997 |
| WO | WO9906981 A1 | 2/1999 |
| WO | WO0235993 A2 | 5/2002 |

* cited by examiner

*Primary Examiner* — Sean Dougherty
(74) *Attorney, Agent, or Firm* — Peter A. Nieves; Sheehan Phinney Bass + Green PA (57) ABSTRACT

Provided are a device, system, and method for treating a patient having posttraumatic stress disorder (PTSD) or other such psychiatric disorder. An event being recounted by the patient is recorded and a sensory environment of the patient is controlled so as to administer exposure therapy to the patient. Patient mental state may be monitored during administration of the exposure therapy to the patient, and the exposure therapy may be varied in correspondence to the monitored mental state of the patient. In one embodiment, hierarchy assembly means creates a treatment hierarchy based on input from the patient, and hierarchy navigation means navigates within the treatment hierarchy in response to the mental state of the patient.

22 Claims, 5 Drawing Sheets

DEVICE, SYSTEM, AND METHOD FOR TREATING PSYCHIATRIC DISORDERS

CROSS-REFERENCE TO RELATED APPLICATION

This application claims priority to U.S. Provisional Patent Application entitled "Psychiatric Disorder Treatment," having Ser. No. 61/079,648, filed 10 Jul. 2008, which is hereby incorporated herein in its entirety by reference.

FIELD OF THE INVENTION

The present invention relates to treatment of psychiatric disorders, and more particularly relates to use of prolonged exposure therapy for treatment of posttraumatic stress disorder and similar psychiatric disorders.

BACKGROUND OF THE INVENTION

Exposure therapy, also referred to by terms including but not limited to "prolonged exposure (PE)," "direct therapeutic exposure," "flooding," "implosive therapy," "graduated exposure," "systematic desensitization," and "exposure and response prevention," but hereafter referred to as "exposure therapy" is a treatment for various psychiatric disorders, psychosocial problems, and conditions (hereinafter referred to for convenience as "psychiatric disorders" but without intention to limit to any particular type or degree of seriousness of condition).

In exposure therapy, a patient displaying symptoms of posttraumatic stress disorder (PTSD) or other such psychiatric disorder as a result of some traumatic or stressful event might, with the aid of a therapist, be repeatedly exposed to imagery and stimuli associated with the traumatic event until the patient becomes desensitized or habituates, such that fear reactions to the imagery and stimuli are extinguished. During imaginal exposure therapy the patient might first be exposed to a memory of an event by orally (or sometimes in writing) recounting the memory repeatedly for a prolonged period, in the therapist's office, thereby evoking the emotional experience of the event, and creating an exposure environment in the therapist's office. Then the patient might replicate exposure to the memory and associated emotions outside the therapy office, using sound, imagery, or other such stimuli, such as, but not limited to, a recording of the patient describing the traumatic event to the therapist that might be used to recreate the exposure environment outside the office of the therapist. During in vivo exposure treatment, the patient might be exposed to stimuli associated with the traumatic event, such as, but not limited to, objects, clothing, persons, smells, sounds, pictures, or locations that elicit emotional distress due to their association with the traumatic event. The patient might be directed, for example, to go to a location at which the traumatic event occurred or to a location reminiscent of the traumatic event, in which case this location would serve as the exposure therapy environment. In either case, repeated and prolonged contact with the exposure imagery and stimuli produces the desensitization or habituation that allows the patient to gradually overcome fear, anxiety, sadness, and other distress associated with the event.

Although exposure therapy has been shown to be effective, many individuals with PTSD, anxiety reactions, and other psychiatric disorders never obtain exposure therapy. For example, some individuals may not seek treatment because they do not realize they have a problem, would prefer to solve it on their own, or encounter substantial financial, logistical, or emotional barriers to seeking treatment. In addition, the availability of professionals trained and willing to deliver exposure therapy is limited. It would therefore be desirable to implement exposure therapy by computer to allow automated or partially automated administration of treatment, thus reducing barriers to dissemination and increasing the number of patients capable of receiving treatment.

Conventional virtual reality (VR) programs may provide some degree of computer-assisted exposure therapy. However, the stimuli in such conventional VR programs have typically been created by a computer programmer. That is, conventional VR programs typically contain graphics and audio representing the computer programmer's construction of generic stressful events. Such conventional VR programs are therefore inadequate where it is preferred that the stimuli used for treatment be created by the patients themselves or otherwise be based on the individualized real-world experiences of the patients. There is therefore a need for a computer-assisted exposure therapy creation and delivery system that employs audio and/or video or other media recordings in the voice and/or image of the patient or otherwise incorporates input from the patient to replicate his or her specific traumatic memories.

Thus, a heretofore unaddressed need exists in the industry to address the aforementioned deficiencies and inadequacies.

SUMMARY

Embodiments of the present invention provide a device, system, and method for treating psychiatric disorders.

Briefly described, one embodiment, among others, is a system for treating a patient having a psychiatric disorder. The system may comprise a memory and may further comprise a processor configured by the memory to perform the steps of recording an event experienced by the patient and controlling a sensory environment of the patient so as to administer exposure therapy to the patient. The mental state of the patient may be monitored during administration of the exposure therapy to the patient. Furthermore, the exposure therapy that is administered to the patient may be varied in correspondence to the monitored mental state of the patient.

Another embodiment is a computer system for treating a patient having a psychiatric disorder through use of exposure therapy. The system may comprise patient interface means for providing or directing visual and audio exposure. The system may further comprise sensor means for sensing a level of patient anxiety or distress. The system may further comprise processor means for controlling the providing or directing of visual and audio exposure. Furthermore, the computer may provide or direct the visual and the audio exposure responsive to the level of sensed anxiety or distress.

Another embodiment is a system for treating a patient having a psychiatric disorder. The system may contain a memory and may further contain a processor configured by the memory to perform the steps of monitoring a mental state of the patient; recording an event being recounted by the patient; parsing the event into a plurality of stimuli; controlling a sensory environment of the patient so as to administer exposure therapy to the patient based on at least one of the stimuli; associating, with each of the stimuli on which the exposure therapy is based, a first mental state metric value representative of the monitored mental state of the patient when the patient recounted the stimulus; and associating, with each of the stimuli on which the exposure therapy is based, a second mental state metric value representative of the monitored mental state of the patient when the exposure therapy based on the stimulus was administered to the patient.

The processor may furthermore be configured by the memory to perform the step of varying the sequence of the stimuli on which the exposure therapy is based in correspondence to the second mental state metric value until the second mental state metric value indicates habituation of the patient as compared with the first mental state metric value. Alternatively or in addition, the processor may furthermore be configured by the memory to perform the step of varying the intensity of at least one of the stimuli on which the exposure therapy is based in correspondence to the second mental state metric value until the second mental state metric value indicates habituation of the patient as compared with the first mental state metric value.

In accordance with one embodiment of the invention, the controlled sensory environment may be an imaginal environment. The imaginal environment may be implemented by playing back a recording in the voice and/or image of the patient.

The controlled sensory environment may also be an in vivo environment. The in vivo environment may be implemented through use of a portable computing device that guides the patient to approach and be exposed to at least one of the stimuli. For example, the patient may be guided to enter a location that is the scene of, or that is reminiscent of the scene of, the event, or to otherwise expose himself or herself to objects, persons, smells, sounds, lighting conditions or other such stimuli that evoke emotions related to the traumatic event.

The monitoring for the first and second mental state metric values may include monitoring of self-reported mental state, and/or monitoring of speech, facial affect, and/or at least one biological or physiological characteristic. The at least one biological or physiological characteristic may include at least one species chosen from among the group consisting of breathing, heart rate, blood pressure, peripheral resistance, skin temperature, skin conductance, sweat gland activity, facial electromyographic response, peripheral muscle activity, restlessness, and shifting in chair.

The processor may furthermore be configured by the memory to perform the step of delivering coping statements to the patient in correspondence to the second mental state metric value.

Another embodiment is a psychiatric disorder treatment data structure stored on a computer-readable medium. The data structure may contain a plurality of stimuli parsed from an event recounted by a patient. The data structure may further contain a history of mental state metric values respectively associated with the stimuli. The mental state metric values may respectively indicate monitored mental state of the patient during the recounting of the event by the patient and during at least one instance when at least one of the stimuli was used to administer exposure therapy to the patient.

Another embodiment of the present invention provides a computer-readable medium having stored thereon computer-executable instructions for configuring a processor to perform any of the foregoing steps.

Another embodiment is a system for treating a patient having a psychiatric disorder. The system may comprise a memory and may further comprise a processor configured by the memory to perform the steps of monitoring a mental state of the patient; recording an event experienced by the patient; parsing the event into a plurality of stimuli; associating with each of the stimuli a mental state metric value representative of the monitored mental state of the patient when the patient experienced the stimulus; and identifying one or more of the stimuli as being salient based on the mental state metric value associated with the stimuli.

A further embodiment of the present invention is a psychiatric disorder treatment device containing patient communication means for communicating with and controlling the sensory environment of a patient; patient monitoring means for monitoring a mental state of the patient; hierarchy assembly means for creating a treatment hierarchy based on input from the patient; and hierarchy navigation means for navigating within the treatment hierarchy in response to the mental state of the patient.

Other embodiments, systems, methods, and features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

As used herein, the term "patient" (also referred to as "user") refers to a person to whom treatment is administered by the device, system, and/or method of the present invention. Examples of patients include persons having any of a variety of types of emotional distress, including, without limitation, anxiety disorders (such as, but not limited to, posttraumatic stress disorder, phobias, social anxiety, panic disorder, obsessive compulsive disorder, generalized anxiety, or any other anxiety disorder), sexual dysfunction, unresolved grief, insomnia, or any of a variety of anger or stress-related problems or other psychosocial problems or conditions. Note that the term "psychiatric disorder" is for convenience used herein to refer to any of the foregoing and should not be interpreted as limiting with respect to type or degree of seriousness of condition experienced by the patient. As used herein, the term "therapist" refers to a psychiatrist, psychologist, doctor, healthcare provider, nurse, social worker, counselor, or other such medical professional under whose supervision treatment is administered by the device, system, and/or method of the present invention. As used herein, "exposure therapy" may include prolonged exposure (PE) therapy, exposure and response prevention, graduated exposure, direct therapeutic exposure, flooding, implosive therapy, systematic desensitization, and/or other such exposure-based interventions.

Aspects of the present invention include a device, system, and method for treating psychiatric disorders. Note that where the description below refers to a system for treating psychiatric disorders in accordance with one aspect of the present invention, this description should be understood to apply as well to a device and a method in accordance with other aspects of the present invention with modification as appropriate. The present system may be provided by a Web-based application. The following description assumes that the present system is provided by a Web-based application. It should be noted that the present system may also be provided in an environment that is not Web-based. Specifically, the present system may be provided on a hand-held device, a local computer, or any device having a memory and a processor. In addition, the present system may be provided via a local area network or a wide area network.

The psychiatric disorder treatment system of the invention can be implemented in software (e.g., firmware), hardware, or a combination thereof. In the currently contemplated best mode, the psychiatric disorder treatment system is implemented in software, as an executable program, and is executed by a special or general purpose digital computer, such as a personal computer (PC; IBM-compatible, Apple-compatible, or otherwise), workstation, minicomputer, or mainframe computer. Specifically, the psychiatric disorder treatment system, as provided by the computer, may be accessible via a Web site, through which parties using the psychiatric disorder treatment system may interact. Further description of the psychiatric disorder treatment system, and interaction therewith is provided below.

Figure 1:
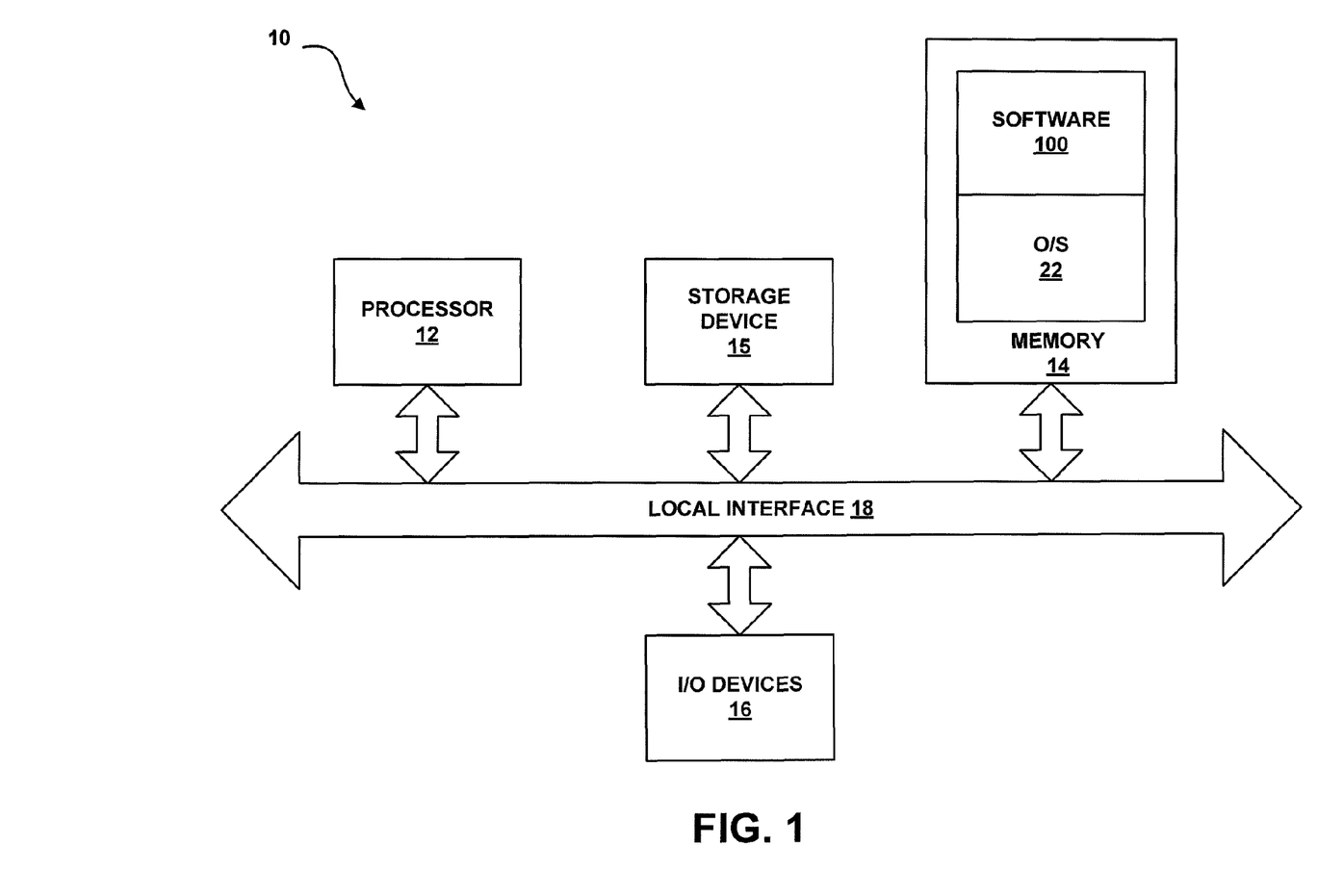
FIG. 1 is a schematic diagram illustrating one example of a general purpose computer for implementing a device, system, and method for treating psychiatric disorders in accordance with a first examplary of embodiment of the present invention.

An example of a general purpose computer that can implement the psychiatric disorder treatment system of the present invention is shown in FIG. 1. In FIG. 1, the psychiatric disorder treatment system implemented by the computer is denoted by reference numeral 10. It should be noted that communication with the psychiatric disorder treatment system may be provided by multiple means such as, but not limited to, the Internet. Further description with regard to use of the psychiatric disorder treatment system via use of the Internet is provided below.

Generally, in terms of hardware architecture, as shown in FIG. 1, the computer 10 includes a processor 12, memory 14, storage device 15, and one or more input and/or output (I/O) devices 16 (or peripherals) that are communicatively coupled via a local interface 18. The local interface 18 can be, for example but not limited to, one or more buses or other wired or wireless connections, as is known in the art. The local interface 18 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 12 is a hardware device for executing software, particularly that stored in the memory 14. The processor 12 can be any custom made or commercially available processor, a central processing unit (CPU), an auxiliary processor among several processors associated with the computer 10, a semiconductor based microprocessor (in the form of a microchip or chip set), a macroprocessor, or generally any device for executing software instructions.

The memory 14 can include any one or combination of volatile memory elements (e.g., random access memory (RAM, such as DRAM, SRAM, SDRAM, etc.)) and nonvolatile memory elements (e.g., ROM, hard drive, tape, CDROM, DVD, flash memory, solid-state memory, etc.). Moreover, the memory 14 may incorporate electronic, magnetic, optical, and/or other types of storage media. Note that the memory 14 can have a distributed architecture, where various components are situated remote from one another, but can be accessed by the processor 12.

The software 100 in memory 14 may include one or more separate programs, each of which contains an ordered listing of executable instructions for implementing logical functions of the psychiatric disorder treatment system, as described below. In the example of FIG. 1, the software 100 in the memory 14 defines the psychiatric disorder treatment system functionality in accordance with the present invention. In addition, the memory 14 may contain an operating system (O/S) 22. The operating system 22 essentially controls the execution of computer programs and provides scheduling, input-output control, file and data management, memory management, and communication control and related services.

Instructions for implementing the psychiatric disorder treatment system 10 may be provided by a source program, executable program (object code), script, or any other entity containing a set of instructions to be performed. When a source program, the program needs to be translated via a compiler, assembler, interpreter, or the like, which may or may not be included within the memory 14, so as to operate properly in connection with the operating system 22. Furthermore, instructions for implementing the psychiatric disorder treatment system 10 can be written as (a) an object oriented programming language, which has classes of data and methods, or (b) a procedure programming language, which has routines, subroutines, and/or functions.

The I/O devices 16 may include input devices, for example but not limited to, a keyboard, mouse, touch screen, scanner, biosensor, microphone, other computing device, etc. Furthermore, the I/O devices 16 may also include output devices, for example but not limited to, a printer, display, etc. Finally, the I/O devices 16 may further include devices that communicate via both inputs and outputs, for instance but not limited to, a modulator/demodulator (modem; for accessing another device, system, or network), a radio frequency (RF) or other transceiver, a telephonic interface, a bridge, a router, etc.

In accordance with the present invention, the I/O devices 16 may also include devices capable of detecting psychological characteristics of a user or patient. Examples of such devices 16 may include, but are not limited to, devices for detecting heart rate, skin conductance, sweat gland activity, muscle activity or other physiological responses, devices for analyzing voice quality, devices for analyzing speech content, and devices for analyzing facial expression. It should be noted that functionality for performance of I/O devices capable of detecting physiological characteristics of a user or patient may be stored within a device separate from the computer, but connected to the computer, or may be stored within the memory 14 of the computer.

Figure 2:
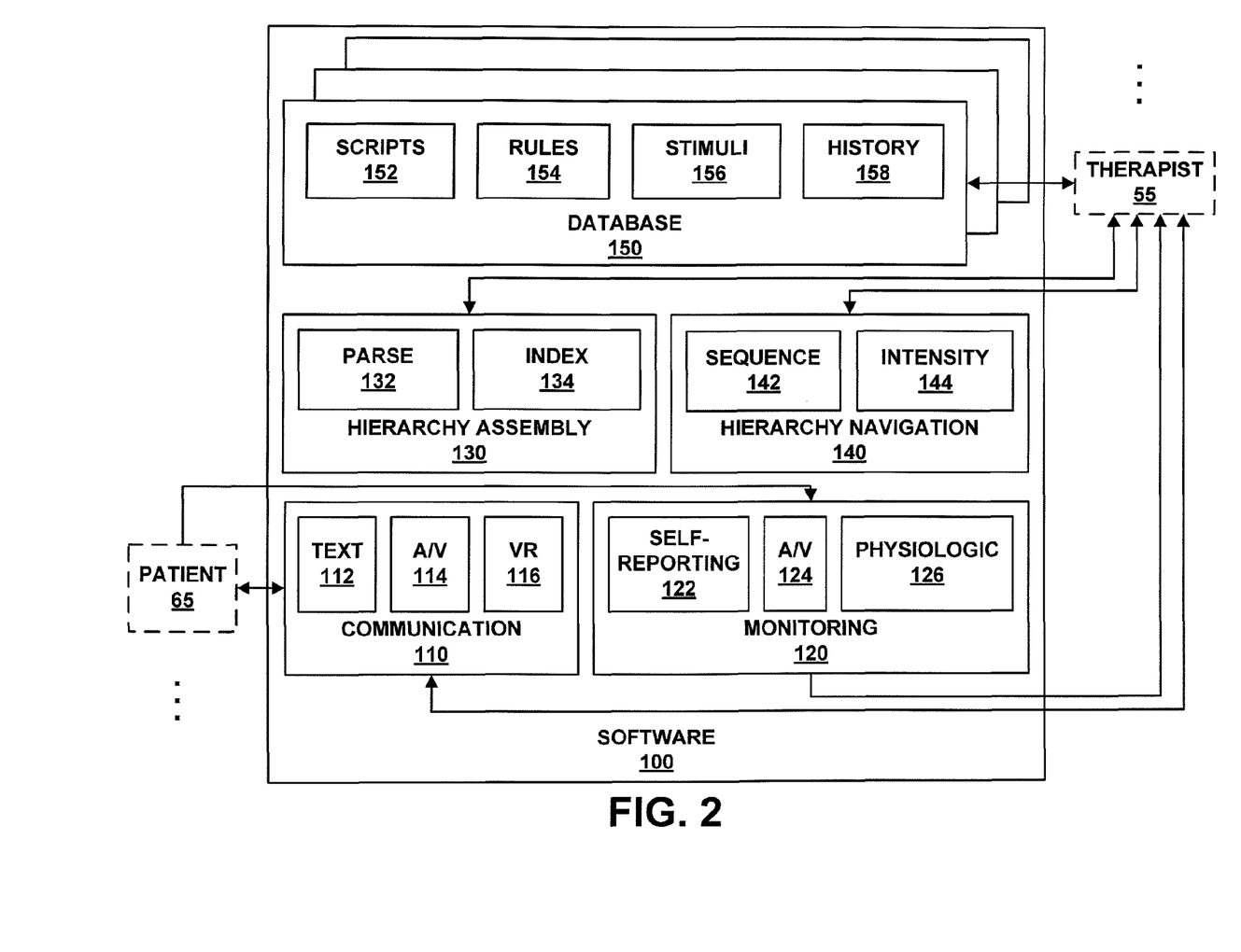
FIG. 2 is a schematic diagram illustrating functional blocks representing functionality defined by the software of FIG. 1, in accordance with a first exemplary embodiment of the present invention.

In summary, regarding I/O devices 16, the exemplary embodiment may, for example, provide a video screen for displaying a graphical environment and a speaker for delivering sound for communicating with the patient 65 (FIG. 2). Additionally, the present system may use a variety of other suitable devices to communicate with the patient 65 (FIG. 2).

The exemplary embodiment may also use a variety of sensors to track the current health and/or mental status of the patient 65 (FIG. 2), for example, level of anxiety via pulse, voice, facial expressions, skin conductance, muscle tension.

When the functionality of the psychiatric disorder treatment system 10 is in operation, the processor 12 is configured to execute the software 100 stored within the memory 14, to communicate data to and from the memory 14, and to generally control operations of the computer 10 pursuant to the software 100. The psychiatric disorder treatment system 10 and the operating system 22, in whole or in part, but typically the latter, are read by the processor 12, perhaps buffered within the processor 12, and then executed.

When the psychiatric disorder treatment system 10 is implemented in software, as is shown in FIG. 1, it should be noted that instructions for implementing the psychiatric disorder treatment system 10 can be stored on any computer-readable medium for use by or in connection with any computer-related device, system, or method. Such a computer-readable medium may, in some embodiments, correspond to either or both the memory 14 or the storage device 15 shown in FIG. 1. In the context of this document, a computer-readable medium is an electronic, magnetic, optical, or other physical device or means that can contain or store a computer program for use by or in connection with a computer-related device, system, or method. Instructions for implementing the psychiatric disorder treatment system 10 can be embodied in any computer-readable medium for use by or in connection with the processor 12 or other such instruction execution system, apparatus, or device. Although the processor 12 has been mentioned by way of example, such instruction execution system, apparatus, or device may, in some embodiments, be any computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the processor 12 or other such instruction execution system, apparatus, or device.

Such a computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the psychiatric disorder treatment system 10 is implemented in hardware, the psychiatric disorder treatment system 10 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Although not shown at FIG. 1, one or more patients 65 (FIG. 2) may be communicatively connected to one or more of the I/O devices 16. Moreover, although not shown at FIG. 1, one or more therapists 55 (FIG. 2) may be communicatively connected to one or more of the I/O devices 16. Note that in at least one embodiment a therapist 55 need not be present, it being possible for a patient 65 to employ the present invention for self-help. In embodiments in which there is at least one patient 65 (FIG. 2) and at least one therapist 55 (FIG. 2), respectively, communicatively connected to I/O devices 16, the at least one patient 65 (FIG. 2) and the at least one therapist 55 (FIG. 2) may be at the same or at different sites. That is, although the I/O devices 16, the local interface 18, the processor 12, the storage device 15, and the memory 14, including operating system 22 and software 100, are respectively shown as single blocks in FIG. 1, any of these may represent one or more blocks thereof In particular, inasmuch as there may be multiple patients 65 (FIG. 2) and/or therapists 55 (FIG. 2) at multiple sites, there may be multiple local interfaces 18 handling communications by site, patient and/or therapist. Moreover, one or more networks, including local area networks (LANs), wide area networks (WANs), and/or global computer networks such as the Internet (also popularly known as "the Web"), may mediate communication between any of the components shown in FIG. 1, or between any of the components shown in FIG. 1 and any entity not explicitly shown in FIG. 1 (e.g., patient(s) 65 (FIG. 2) and/or therapist(s) 55 (FIG. 2)). As one example, the invention may be carried out in the context of cloud computing.

Referring to FIG. 2, this is a schematic diagram illustrating functional blocks representing functionality defined by the software 100 of FIG. 1, and interaction with the software 100, in accordance with a first exemplary embodiment of the invention. In accordance with the present embodiment, the software 100 includes a patient communication module 110, a patient monitoring module 120, a hierarchy assembly module 130, a hierarchy navigation module 140, and a memory storage 150. At FIG. 2, dots are shown next to the patient 65 and the therapist 55 so as to imply presence in some embodiments of multiple patients 65 and/or multiple therapists 55 connected to the same psychiatric disorder treatment system 10, in accordance with an embodiment of the invention. Note that in at least one embodiment a therapist 55 need not be present, it being possible for a patient 65 to employ the present invention for self-help.

The patient communication module 110 may include functionality for communicating with the patient 65. As used herein, communication with the patient 65 may include controlling the environment of the patient 65 during playback of events. In accordance with one embodiment, such communication may be between the patient 65 and the therapist 55 or may be between the patient 65 and the psychiatric disorder treatment system 10. For example, in one embodiment, the patient communication module 110 may permit recording and playback of events recounted by the patient 65 under the control of the therapist 55 and/or under the control of the hierarchy assembly module 130, the hierarchy navigation module 140, or other portions of the software 100. Recording and playback of events as used herein may refer narrowly to the literal recording and playback of events as recounted in the voice and/or image of the patient 65, or may refer more broadly to processed narratives or other such media content that is produced based on events recounted by the patient 65, but that is not necessarily in the voice and/or image of the patient 65, and that may moreover contain supplemental tactile, haptic, olfactory, or other such supplemental sensory content such as that which is sometimes associated with virtual reality (VR). Recording and playback of events as used herein may also refer to recording of actual events experienced by the patient and playback of stimuli extracted therefrom. For example, in one embodiment, automated recording of everyday experiences undergone by a patient wearing a portable monitor and a recording device might be carried out.

It should be noted that one embodiment of the psychiatric disorder treatment system 10 is different from VR in the sense that the treatment session in the embodiment employs events recounted by the patient 65, whether those events are played back in the actual voice and/or image of the patient 65 or whether processed narratives or other media content based on the events recounted by the patient 65 are played back to the patient 65, rather than a computer-simulated environment that has been separately prepared or has otherwise not been generated based on events recounted by the patient 65. However, it should be noted that one embodiment of the psychiatric disorder treatment system 10 may employ tactile, haptic, olfactory, or other such supplemental sensory content.

Furthermore, in an embodiment where it is processed narratives or other such media content based on the events recounted by the patient 65 rather than the events themselves (or stimuli extracted from those events) as actually experienced by the patient or as actually recounted in the voice and/or image of the patient 65 that are played back to the patient 65, the events employed during the treatment session could in such case be said to have a virtual as well as an actual component. That is, in some embodiments, there is no particular objection to use of sensory stimuli other than auditory or visual stimuli or even use of certain technology associated with VR to create what may be a partially synthesized environment in which the patient may be immersed, but where this is done, the patient environment created in accordance with embodiments of the present invention will have been created based on the actual experiences of the patient as recounted by the patient and will therefore benefit from input from the patient.

For example, a text-based communication module 112 in one embodiment may permit communication with the patient 65 by means of a keyboard and display. Furthermore, an audiovisual communication module 114 in one embodiment may permit communication with the patient 65 by means of a webcam setup permitting audiovisual communication through use of a microphone, speaker, video camera, and display screen. Moreover, a virtual reality communication module 116 in one embodiment may permit communication with the patient 65 by means of tactile, haptic, olfactory, or other such sensory content intended to supplement text-based and/or audiovisual content. Note that where the term "VR" or "virtual reality" is employed in connection with embodiments of the present invention, this is meant to refer to use of sensory stimuli other than auditory or visual stimuli to create a patient environment that may be partially synthesized but that has nonetheless been created based on the actual experiences of the patient as recounted by the patient, as distinguished from certain conventional VR environments that are not based on the actual experience of the patient but have instead been created based on the imagination of a computer programmer or based on a supposed generic narrative presumed to apply to the patient but without the benefit of actual input from the patient. It should be noted that there is no requirement for use of "VR" in the present invention.

In general, communication with the patient 65 may be one-way (unidirectional) or two-way (bidirectional). In an embodiment in which communication is two-way (bidirectional), this need not mean that communication occurs in both directions simultaneously. For example, in some embodiments or at some times, the text-based communication module 112 or the audiovisual communication module 114 may permit simultaneous two-way text-based or audiovisual communication, e.g., when the therapist 55 and the patient 65 are in direct communication; but in other embodiments or at other times, the text-based communication module 112 or the audiovisual communication module 114 may only allow one-way text-based or audiovisual communication, e.g., one-way communication from the patient 65 to the psychiatric disorder treatment system 10 during recording of events, and one-way communication from the psychiatric disorder treatment system 10 to the patient 65 during playback of events. Where the virtual reality communication module 116 is present, it will typically be used during playback of events.

In one embodiment in which the text-based communication module 112 or the audiovisual communication module 114 employs a video screen placed in front of the patient 65 to communicate with the patient 65, the video screen may be used by the psychiatric disorder treatment system 10 to display an image of a virtual therapist, written instructions, and/or other interactive media images that are intended to facilitate the experience of anxiety and/or sadness within the patient as relevant to the particular patient problem. Moreover, in an embodiment in which the text-based communication module 112 or the audiovisual communication module 114 employs a headset worn by the patient 65 to communicate with the patient 65, the headset may be used by the psychiatric disorder treatment system 10 to allow the patient 65 to record audio descriptions of relevant imagery material and to listen to audio material that corresponds to information provided on the video screen.

The patient monitoring module 120 may include functionality for monitoring the mental state of the patient 65. Specifically, in one embodiment, by monitoring of "mental state," it is meant that the level of anxiety or distress of the patient 65 is monitored. For example, the patient monitoring module 120 might include a self-reporting module 122, an audiovisual module 124, and/or a physiologic module 126.

Note that the term "mental state" as used herein should be understood broadly to include not only qualities and characteristics associated with mental function per se, but also any of a wide range of qualities, characteristics, and phenomena that might in other contexts be associated with emotional state or even physiological state. One representative example of what might in other contexts be considered a physiological state but which should in the context of the present invention be considered as a possible example of mental state would, for example, be muscle tension, such as stiffness in the area of the shoulders or neck, as such ostensibly physiological phenomena might in some cases be associated with or indicative of the mental state of the patient.

The self-reporting module 122, where present, might allow the patient 65 to self-report what the patient 65 perceives to be his or her current mental state. For example, the patient 65 might be asked to indicate his or her current level of anxiety, stress, or distress at regular intervals, e.g., every 2 minutes. Such self-reported indication of current mental state may, for example, be as indicated on a subjective units of distress scale (SUDS). Such a scale might, for example, contain a range from 1 to 10 and be in answer to a question such as, "How much anxiety are you currently feeling?", where a response of 1 might indicate "none at all" and a response of 10 might indicate "the worst imaginable anxiety". The self-reporting module 122 possesses functionality allowing the patient 65 to self-report current mental state by any of a variety of methods including keyboard entry, joystick, voice or other audible sign, or gesture or other visible sign. Where self-reported mental state is monitored using audio equipment to detect the spoken response of the patient 65, voice recognition processing may be employed to convert the audible response of the patient 65 to data that is more readily converted into a mental state metric. Where self-reported mental state is monitored using video equipment to detect the gesture or signed response of the patient 65, image processing may be employed to convert the visible response of the patient 65 to data that is more readily converted into a mental state metric.

The audiovisual monitoring module 124, where present, might include a webcam setup or other such equipment for monitoring the speech and/or facial expressions of the patient 65 and generating a mental state metric based thereon.

Monitoring of the speech of the patient 65 by the audiovisual monitoring module 124 may include monitoring of the logical or emotional content of what the patient 65 says and/or may include monitoring of the way in which the patient 65 produces speech. For example, voice recognition and/or linguistic analysis may be employed during monitoring of the logical or emotional content of what the patient 65 says. Furthermore, audio signal processing may be carried out to monitor aspects of the way in which the patient 65 produces speech, such aspects including, for example, speech patterns, breathing as it affects speech, whether speech is relaxed or pressured, and tightness of vocal cords.

Monitoring of the facial expressions of the patient 65 by the audiovisual monitoring module 124 may include image processing techniques that detect and analyze facial reactions or other such changes in facial musculature to determine the emotion or state of mind (hereinafter "facial affect") of the patient 65.

The physiologic module 126, where present, may include any of various sensors designed to measure biological or physiological phenomena or parameters correlatable to the emotion or state of mind of the patient 65. Especially suitable for monitoring by the physiologic module 126 in the context of embodiments of the present invention are phenomena indicative of nervousness, stress, anxiety, distress, or similar emotional state. For example, any of the biological or physiological parameters typically measured during a so-called lie detector test might be measured during monitoring of the patient 65 and received by the physiologic module 126 in the context of embodiments of the present invention. Examples of such biological or physiological parameters that may be measured through use of suitable sensors during monitoring by the physiologic module 126 include breathing, heart rate, blood pressure, other aspects of the cardiovascular system, sweat gland activity (e.g., skin conductance), and muscle activity in areas such as the facial muscles or other parts of body. For example, a physiologic module 126 in one embodiment might monitor heart rate and/or skin conductance of the patient 65 through use of a finger- or earlobe-clip probe or other suitable monitoring device. Furthermore, the physiologic module 126 in some embodiments might monitor any of a wide variety of other activities or phenomena that could provide clues to the therapist 55 regarding the mental state of the patient 65. Such activities and phenomena include various patient behaviors that might catch the attention of a therapist during a conventional face-to-face session with a patient. As one example, a sensor beneath a seat cushion might be employed by the physiologic module 126 in one embodiment to monitor shifting around by the patient 65 in his or her chair.

The patient monitoring module 120 may furthermore include functionality for generating a mental state metric indicative of the monitored mental state of the patient 65. The mental state metric may be a number or set of numbers, a letter grade or set of letter grades, or any other symbolic representation or set of representations indicative of the mental state of the patient 65.

Where the patient 65 is monitored by the patient monitoring module 120 in more than one way, it is preferred that the patient monitoring module 120 integrate, compare, contrast, reconcile, or otherwise reflect the results of monitoring from the various means employed before generating a mental state metric indicative of the mental state of the patient 65. For example, one embodiment might employ a self-reporting module 122, an audiovisual monitoring module 124, and a physiologic module 126. Another embodiment might employ a physiologic module 126 making use of multiple sensors to detect multiple biological or physiological parameters. Still another embodiment might employ an audiovisual monitoring module 124 to monitor both the speech and the facial affect of the patient 65. In such situations where multiple measures of patient mental state are available, divergences or inconsistencies between or among monitored parameters, particularly as compared with self-reported mental state as reported by the patient 65 by way of the self-reporting module 122 (i.e., in an embodiment where such a self-reporting module 122 is present), can provide valuable clues as to the mental state of the patient 65. For example, use of the audiovisual monitoring module 124 and/or the physiologic module 126 as a check on patient mental state as self-reported by the patient 65 by way of the self-reporting module 122 can help to uncover any reporting bias or other calibration-like issues, especially those that are attributable to or would provide insight regarding the mental state of the patient 65.

The hierarchy assembly module 130 may include functionality for assembling a treatment hierarchy containing stimuli and associated indexing information. Such hierarchy assembly functionality may for example be employed during recording of events, recording of events being as defined below. In one embodiment, the hierarchy assembly module 130 includes a parsing module 132 and an indexing module 134.

The parsing module 132 in one embodiment has functionality for extracting one or more stimuli from an event. For example, an event recounted by the patient may be parsed or divided into segments serving as stimuli for later playback to the patient. Besides such segments, other examples of classes of stimuli include media content, objects, locations, activities, people, smells, tastes, lighting and other ambient conditions, and colors (e.g., camouflage).

The indexing module 134 in one embodiment has functionality for associating with a stimulus the mental state metric generated by the patient monitoring module 120 at the time that the stimulus is being experienced or recounted by the patient 65 and/or at the time that the stimulus is being played back to the patient 65. The indexing module 134 may alternatively or in addition have functionality for associating with a stimulus, information indicating the chronological or logical sequence of the stimulus within the event as it was recounted by the patient 65. In one embodiment, stimuli 156 and associated history 158 of mental state metric values and/or history of times at which the stimuli were recorded and/or played back (hereinafter "session history") are stored in the storage device 15.

The hierarchy navigation module 140 may include functionality for navigating within the framework of one or more treatment hierarchies. Such hierarchy navigational functionality may for example be employed during playback of events, playback of events being as defined below. In one embodiment, the hierarchy navigation module 140 includes a sequence module 142 and an intensity module 144. In a preferred embodiment, the sequence module 142 has functionality for ordering stimuli in a suitable sequence within a treatment hierarchy, or adjusting the sequence of the stimuli within such a treatment hierarchy, based on patient mental state and/or session history. Specifically, the sequence module 142 in one embodiment might cause playback of a stimulus to be repeated until it is determined that the patient 65 has habituated sufficiently to that stimulus. Similarly, in a preferred embodiment, the intensity module 144 has functionality for setting playback intensity of a stimulus to a level expected to be suitable within a treatment hierarchy, or adjusting the playback intensity of a stimulus within such a treatment hierarchy, based on patient mental state and/or session history. Specifically, the intensity module 144 in one embodiment might cause playback intensity for a stimulus to be set to increasingly higher levels until it is determined that the patient 65 has habituated sufficiently to that stimulus.

Although the hierarchy assembly module 130 has been described as having functionality for assembling treatment hierarchies, and the hierarchy navigation module 140 has been described as having functionality for navigating within treatment hierarchies, in some embodiments the hierarchy assembly module 130 and the hierarchy navigation module 140 may cooperate such that navigation functionality is available to the hierarchy assembly module 130 during hierarchy assembly and/or hierarchy assembly functionality is available to the hierarchy navigation module 140 during hierarchy navigation. For example, during recording of events in accordance with a flowchart of FIG. 4, it may be advantageous to employ hierarchy navigation functionality to navigate within the framework of a treatment hierarchy as it is in the progress of being assembled. Similarly, during playback of events in accordance with a flowchart of FIG. 5, it may be advantageous to employ hierarchy assembly functionality to further fill in and/or modify a treatment hierarchy as it is in the process of being navigated.

Various types of data used during creation and/or administration of treatment hierarchies may be stored at the storage device 15 of FIG. 1, or even in the memory 14. If stored within the memory 14, the memory 14 may have a memory storage 150. For example, the memory storage 150 may contain patient communication scripts 152, hierarchy assembly and navigation rules 154, recorded stimuli 156, and a patient monitoring history 158. In one embodiment, the therapist 55 can review and/or modify the content of the scripts 152, rules 154, stimuli 156, and monitoring/session history 158.

Figure 3:
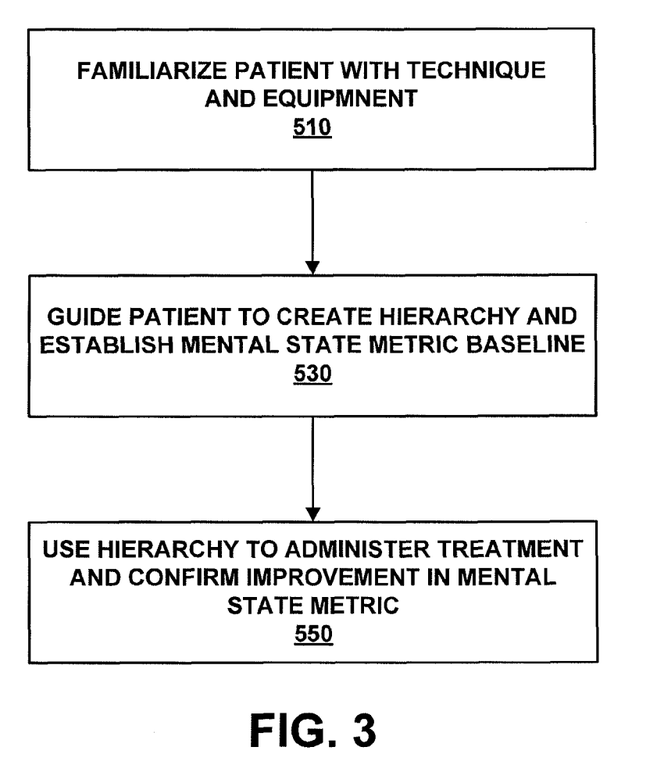
FIG. 3 is a flowchart illustrating a method for treating psychiatric disorders, in accordance with the first embodiment of in FIGS. 1 and 2.

Referring to FIG. 3, this is a flowchart showing a method for treating psychiatric disorders in accordance with the first embodiment of the present invention. As shown by block 510, the patient 65 is familiarized with the technique employed by the psychiatric disorder treatment system 10 of the present invention as well as with the equipment used by the system 10. This step may be carried out entirely automatically, may be carried out entirely manually, or may be carried out partially automatically and partially manually. When carried out manually, the system 10 may allow the therapist 55 to communicate directly with the patient 65 by way of the text-based communication module 112 and/or the audiovisual communication module 114. When carried out automatically, scripts 152 stored in the memory storage 150, such as, in the form of an interactive media program, might be used by the system 10 to educate the patient 65 about common reactions to trauma and PTSD as well as the rationale for prolonged imaginal and in vivo exposure. For example, communication with the patient 65 here may take place through utilization of text and/or animation, and may include oral instructions to the patient 65 as well as feedback from the patient 65.

As shown by block 530, the patient 65 is guided to create one or more exposure therapy hierarchies. In the vernacular of the psychiatric disorder treatment system 10, this is loosely referred to as "recording" of events. This may be carried out entirely automatically, may be carried out entirely manually, or may be carried out partially automatically and partially manually. When carried out manually, the system 10 may allow the therapist 55 to communicate directly with the patient 65 by way of the text-based communication module 112 and/or the audiovisual communication module 114, at which time one or more of prompting of the patient 65 to recount an event, indexing and organization of stimuli into a hierarchy, and storage of the hierarchy at the memory storage 150 would be carried out under the control of the therapist 55. When carried out automatically, scripts 152 may be used to prompt the patient 65 to recount an event under the control of the hierarchy assembly module 130, indexing and organization of stimuli into a hierarchy may be carried out under the control of the hierarchy assembly module 130, and the hierarchy may be stored at the database 150 under the control of the hierarchy assembly module 130.

When carried out partially automatically and partially manually, processing may be as described for automatic creation of exposure therapy hierarchies, except that the therapist 55 would have the ability to override one or more automatic aspects of operation.

For example, in one embodiment, the hierarchy assembly module 130 and/or the hierarchy navigation module 140 may ordinarily operate automatically by using scripts 152 stored in the memory storage 150 to guide the patient 65 during recording and playback of stimuli pursuant to rules 154 stored in the memory storage. Similarly, parsing and indexing of stimuli for creation of hierarchies may ordinarily be carried out automatically by the hierarchy assembly module 130. Moreover, adjustment of sequence and intensity of stimuli for playback of hierarchies may ordinarily be carried out automatically by the hierarchy navigation module 140. However, where this is the case, it is preferred that the therapist 55 be able at any time to override such automatic functionality and temporarily control or redirect hierarchy assembly or navigation as carried out by the hierarchy assembly module 130 or the hierarchy navigation module 140.

For example, in a networked embodiment in which a single therapist 55 oversees administration of treatment to multiple patients 65, automated functionality would allow a default set of scripts 152 as well as standard rules 154 to be employed for hierarchy assembly and navigation so as to free up the time of the therapist 55 where possible, while still allowing the therapist 55 to fine-tune or otherwise adjust the scripts 152 and rules 154 as necessary for special cases. This allows the therapist 55 to, for example, periodically redirect the focus of the hierarchy assembly module 130 or the hierarchy navigation module 140 to topics or events that the therapist 55 wishes to dwell on at greater length or in greater detail. For example, in one embodiment, automatic creation of hierarchies by the hierarchy assembly module 130 might be interrupted by the therapist 55 so as to afford the therapist 55 a chance to confirm content of a treatment hierarchy prior to use of that hierarchy to treat the patient 65. Ability of the therapist 55 to interact with, intervene in, or override automatic processing in some embodiments makes it possible for the therapist 55 to more closely supervise treatment and allows the therapist 55 greater control over treatment administration.

Furthermore, as shown by block 530, as the patient 65 is being prompted to recount an event, and stimuli are being indexed by mental state metric and organized into a hierarchy, this initial value of the mental state metric for each stimulus can serve as a baseline against which desensitization of the patient 65 with respect to that stimulus can later be measured.

As shown by block 550, the patient 65 is guided through a course of imaginal, in vivo, hybrid, or other type of exposure therapy. In the vernacular of the psychiatric disorder treatment system 10, this is loosely referred to as "playback" of events. At this time, the psychiatric disorder treatment system 10 might control specific exposure instructions and/or imagery material delivered to the patient 65 during exposure therapy based on relevant parameters representative of the reactions of the patient 65. For example, one or more sensors may be provided to automatically detect a level of anxiety of the patient 65, with the psychiatric disorder treatment system 10 monitoring such sensors and controllably manipulating the specific exposure instructions and/or imagery material in correspondence thereto.

In one embodiment, at any of the foregoing blocks 510, 530, 550, an alarm might be sent to the therapist 55 or other party, with automatic processing optionally being suspended until the therapist 55 can respond, in certain situations. In one embodiment, such situations might include any time on demand by the patient 65, when heart rate or other such physiologic indicator or other mental state metric reaches a predetermined threshold value, at critical points in stimulus recording or playback, or at any other point where the judgment of a therapist 55 is desirable, e.g., confirmation of the treatment hierarchy created by the hierarchy assembly module 130 prior to use of that hierarchy to treat the patient 65.

Figure 4:
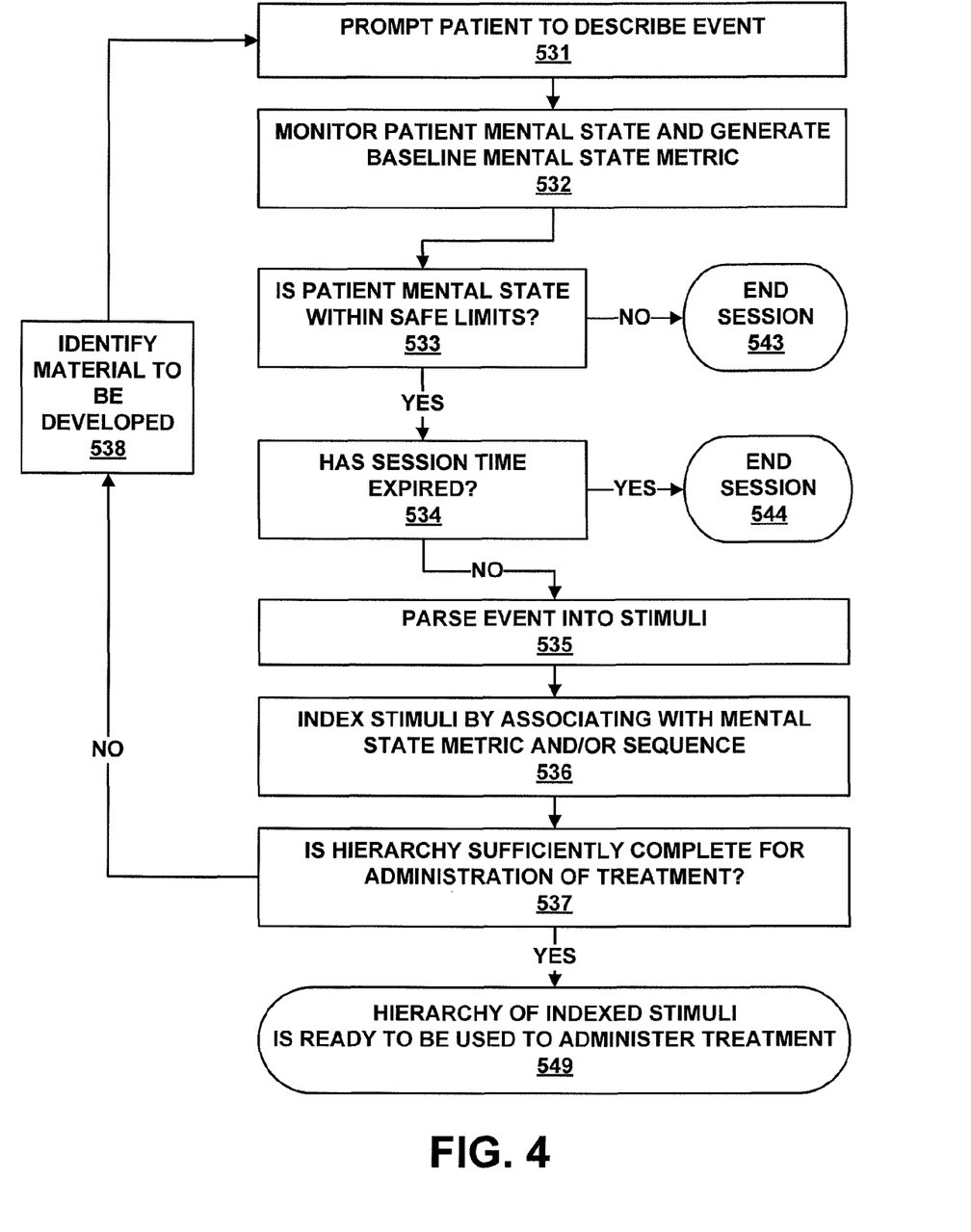
FIG. 4 is a flowchart illustrating a method for recording events recounted by a patient as part of the treatment method of FIG. 3.

FIG. 4 is a flowchart of a method for recording events experienced or recounted by a patient 65 and organizing stimuli extracted from those events into a treatment hierarchy as part of the method for treating psychiatric disorders shown in the flowchart of FIG. 3. Note that as used herein, "recording" may refer literally to creation of an analog or digital record of events (or stimuli extracted from events) as actually experienced by the patient or as actually recounted in the voice and/or image of the patient 65, or may refer more loosely to creation of a logical or emotional narrative or other such media content that has been produced based on the events experienced or recounted by the patient 65. Furthermore, note that the term "recording" as used herein is not limited to such creation as carried out in the context of imaginal treatment, in vivo treatment, hybrid treatment (e.g., certain treatments employing VR technology), or treatments not easily classified as imaginal or in vivo, such as, for example, treatments employing ecological momentary assessment. For example, "recording" as used herein may refer to cataloging or noting of scenes of events when specific exposure instructions are to be used to guide the patient to enter such locations in the context of in vivo treatment or treatments employing ecological momentary assessment. That is, whether treatment is imaginal, in vivo, or something else, the patient is made to experience or recount an event, and exposure therapy based on the experienced or recounted event is administered to the patient, with the creation of a record of the experienced or recounted event being referred to loosely herein as "recording" regardless of whether the record that is created is a literal record or is merely derived from the experienced or recounted event.

As shown by block 531, the patient 65 is, for example, prompted to describe an event. At this time, the therapist 55 might prompt the patient 65 directly by way of the patient communication module 110. Alternatively or in addition, the hierarchy assembly module 130 may, in accordance with rules 154 stored in the memory storage 150, use scripts 152 to prompt the patient 65 by way of the patient communication module 110. Prompting of the patient 65 at this time preferably occurs by way of the text-based communication module 112 or the audiovisual communication module 114 of the patient communication module 110. For example, the patient 65 might be prompted to describe a traumatic experience orally, at which time a microphone could be employed to record the oral description of the patient 65, with prompting to elaborate as appropriate.

As shown by block 532, the patient monitoring module 120 monitors the mental state of the patient 65 and generates a baseline mental state metric. During recording of events experienced or recounted by the patient 65, the mental state metric generated by the patient monitoring module 120 is referred to as a baseline mental state metric since it will be used as a reference against which to compare and monitor progress of the patient 65 during playback of events when treatment is administered as described below with reference to FIG. 5.

Monitoring of the mental state of the patient 65 at this time may include self-reporting by way of the self-reporting module 122, monitoring of speech and/or facial affect by way of the audiovisual monitoring module 124, and monitoring of any of various biological or physiological phenomena by way of the physiologic module 126. The mental state metric generated by the patient monitoring module 120 preferably reflects multiple measures of patient mental state as measured independently in different ways by the patient monitoring module 120. The patient monitoring module 120 stores the results of monitoring and/or the mental state metric in the form of a monitoring history 158 in the memory storage 150.

As shown by block 533, the mental state metric generated by the patient monitoring module 120 is evaluated to determine whether the mental state of the patient 65 is within safe limits. In the event that the mental state metric indicates that further recording of events might be unsafe for the patient 65, the session is ended (block 543). Conversely, if the mental state metric is within safe limits, processing proceeds.

As shown by block 534, a determination is made as to whether the amount of time set aside for the session has expired. For example, to avoid overtiring the patient 65, a predetermined maximum amount of time might be set in advance for the session. In the event that the time set aside for the session has expired, the session is ended at block 544. Conversely, if the time set aside for the session has not yet expired, processing proceeds.

Within the safe limits employed for evaluation of the mental state metric at block 533, there will in general be a range of mental state metric values that can be associated with various stimuli within the event being recounted by the patient 65. One goal of recording of events in accordance with the flowchart of FIG. 4 is to develop a treatment hierarchy containing a series of stimuli that are respectively associated with a range of mental state metric values. In particular, stimuli associated with mental state metric values indicative of distress or anxiety on the part of the patient 65 may be targeted for use during event (stimulus) playback as described below with reference to FIG. 5. By assembling a hierarchy containing an assortment of stimuli associated with a range of mental state metric values, it will be possible during playback to vary the environment of the patient 65 in such a way as to foster habituation in accordance with the goals of exposure therapy as intended by the therapist 55.

As shown by block 535, as the patient 65 is prompted to recount an event by the patient communication module 110 and is monitored by the patient monitoring module 120, the parsing module 132 of the hierarchy assembly module 130 in one embodiment of the present invention parses or divides the event being recounted by the patient 65 into one or more stimuli. Such parsing may be carried out automatically by the parsing module 132 in correspondence to changes in mental state metric or passage of time, or in correspondence to changes in topic as determined by linguistic analysis, for example, or may be carried out manually with intervention from the therapist 55.

Moreover, as shown by block 536, the indexing module 134 of the hierarchy assembly module 130 in such an embodiment associates with each such parsed stimulus the mental state metric generated by the patient monitoring module 120 at the time that the stimulus was being recounted by the patient 65. This mental state metric value is stored in the monitoring history 158 and preferably integrates or otherwise reflects self-reported mental state as monitored by way of the self-reporting module 122, mental state as indicated by speech and/or facial affect as monitored by way of the audiovisual monitoring module 124, and/or mental state as indicated by physiological parameters as monitored by way of the physiologic module 126. In one embodiment, such information associated with the stimulus by the indexing module 134 might alternatively or in addition include information indicating the chronological or logical sequence of the stimulus within the event as it was recounted by the patient 65. In the present embodiment, the hierarchy assembly module 130 stores the stimuli 156 and associated indexing information in the memory storage 150. Thus, the hierarchy assembly module 130 in the present embodiment is able to identify and extract the most salient stimulus or stimuli from the event experienced or recounted by the patient based on mental state metric value.

As shown by block 537, a determination is made as to whether the stimuli 156 and associated indexing information stored in the memory storage 150 by the hierarchy assembly module 130 are sufficient to form a treatment hierarchy. In some embodiments this determination might be made manually by the therapist 55. In other embodiments, this determination might be made automatically by the hierarchy assembly module 130. For example, hierarchy assembly might be determined to be complete when a sufficient number of stimuli 156 having associated therewith a sufficiently wide range of mental state metric values have been stored in the database 150. In the event that the stimuli 156 and associated indexing information stored in the memory storage 150 are sufficient to form a treatment hierarchy, processing for recording of events is ended at block 549. Conversely, if the stimuli 156 and associated indexing information stored in the memory storage 150 are insufficient to form a treatment hierarchy, processing proceeds to block 538.

As shown by block 538, subject matter to be developed for completion of the treatment hierarchy is identified, following which processing returns to block 531, where prompting of the patient 65 is carried out based on the identified subject matter. Identification of subject matter to be developed at block 538 may take place in any of a number of ways. For example, in one embodiment, subject matter to be developed might be chosen manually through intervention of the therapist 55. Alternatively or in addition, selection of subject matter for development might take place by trial-and-error in random or haphazard fashion using open-ended questions that prompt the patient 65 to describe events that trouble him or her. In another embodiment, linguistic analysis might be employed to develop topics suggested by responses of the patient 65 during previous iterations of the loop in the flowchart of FIG. 4.

Figure 5:
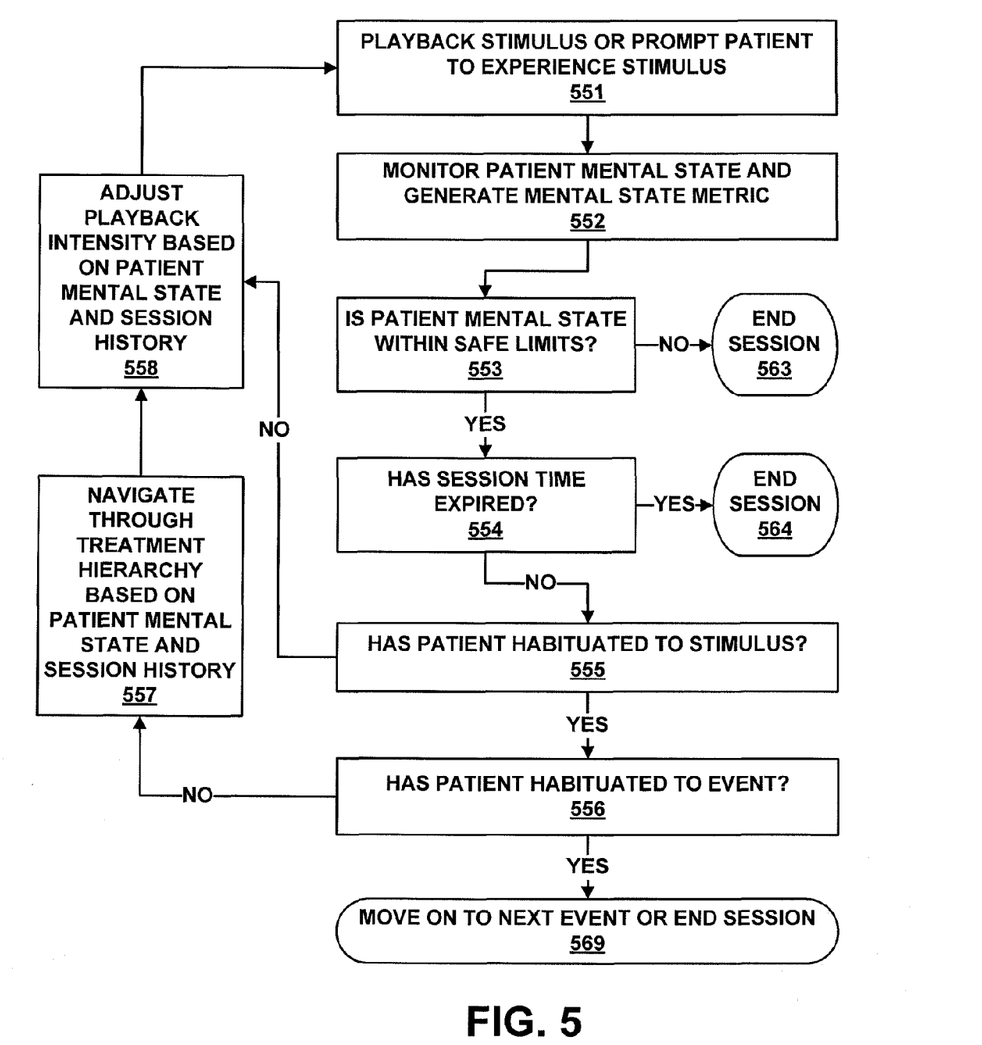
FIG. 5 is a flowchart illustrating a method for playing back events recorded using the event recording method of FIG. 4, as part of the treatment method of FIG. 3.

FIG. 5 is a flowchart illustrating a method for playing back events (or stimuli extracted from events) recorded using the event recording method of FIG. 4 as part of the treatment method of FIG. 3. Note that as used herein, "playback" may refer literally to reproduction of events (or stimuli extracted from events) actually experienced by the patient or a recording in the voice and/or image of the patient 65, or may refer more loosely to delivery to the patient 65 of a logical or emotional narrative or other such media content that has been produced based on an event experienced or recounted by the patient 65. Furthermore, note that the term "playback" as used herein is not limited to such reproduction or delivery as carried out in the context of imaginal treatment, in vivo treatment, hybrid treatment (e.g., certain treatments employing VR technology), or treatments not easily classified as imaginal or in vivo, such as, for example, treatments employing ecological momentary assessment. For example, "playback" as used herein may refer to guiding the patient to enter a location that is or that is reminiscent of the scene of an event in the context of in vivo treatment or treatments employing ecological momentary assessment. That is, whether treatment is imaginal, in vivo, or something else, the patient is made to experience or recount an event, and exposure therapy based on the experienced or recounted event is administered to the patient, with administration of this exposure therapy based on the experienced or recounted event being referred to loosely herein as "playback" regardless of whether the exposure therapy that is administered involves delivery of a literal record of the experienced or recounted event or merely content that is derived therefrom.

As shown by block 551, a stimulus is played back to the patient 65. If imaginal treatment is being carried out, this playback of a stimulus may take the form of reproduction of a recording in the voice and/or image of the patient 65 as the stimulus was recorded in accordance with the flowchart of FIG. 4, or this stimulus playback may take the form of delivery to the patient 65 of a logical or emotional narrative or other such media content that has been constructed based on input from the patient 65, e.g., through use of voice recognition and linguistic analysis processing, or by use of SUDS ratings, physiologic parameters, facial affect regognition and voice quality analyis, which are all indicators of anxiety levels. If in vivo treatment is being carried out, this playback of a stimulus may take the form of prompting to direct the patient 65 to go to a location that is the same as or that is reminiscent of the scene of a traumatic event experienced by the patient 65, or to otherwise expose himself or herself to objects, clothing, persons, smells, sounds, pictures, lighting conditions, or other such stimuli that evoke emotions related to the traumatic event. Note that coping statements may also be communicated to the patient at this time in correspondence to monitored patient mental state; e.g., such coping statements representing guidance from the therapist 55 or system 100 for purposes of encouraging or discouraging certain behaviors of the patient.

Playback of the stimulus at block 551 is preferably carried out by way of the text-based communication module 112 and/or audiovisual communication module 114, with supplemental sensory content optionally being provided to the patient 65 at this time by way of the virtual reality communication module 116, where present.

Furthermore, selection and/or adjustment of the intensity of the stimulus that is played back to the patient 65 at this time may be carried out manually as a result of intervention by the therapist 55, or such selection and/or adjustment of intensity may be carried out automatically under the control of the hierarchy navigation module 140.

In one embodiment, in accordance with rules 154 stored in the memory storage 150, the sequence module 142 of the hierarchy navigation module 140 may select, from among the stimuli 156 stored in the memory storage 150, an stimulus 156 expected to be suitable based on patient mental state and/or session history. For example, because indexing of stimuli 156 by the hierarchy assembly module 130 in one embodiment may result in stimuli 156 being associated with information indicating mental state metric as well as logical or chronological sequence, it is possible, in accordance with the rules 154, for the hierarchy navigation module 140 to select an stimulus 156 that is expected to be suitable based on session history and/or patient mental state. For example, the hierarchy navigation module 140 might at this time select the stimulus 156 that was most anxiety-producing for the patient 65 as determined from the mental state metric values associated with the stimuli 156. Note that the term "sequence" as used herein specifically includes the possibility of repeated use of the same stimulus over and over, such as, until it can be confirmed from the monitored mental state metric that the patient has habituated to the stimulus.

Similarly, in such an embodiment, in accordance with rules 154 stored in the memory storage 150, the intensity module 144 of the hierarchy navigation module 140 may adjust the intensity of the stimulus 156 selected by the sequence module 142 so as to cause playback intensity to be an intensity that is expected to be suitable based on patient mental state and/or session history. For example, because in one embodiment the mental state of the patient 65 as monitored by the patient monitoring module 120 is stored in the memory storage 150 and this mental state metric information is moreover associated with stimuli 156, it is possible, in accordance with the rules 154, for the hierarchy navigation module 140 to adjust the intensity with which an stimulus 156 is played back to the patient 65 so as to be an intensity that is expected to be suitable based on session history and/or patient mental state. Playback intensity as used herein refers to any parameter affecting playback that can be varied so as to increase or decrease the psychological impact, particularly the level of anxiety or distress, that playback of the stimulus has on the patient 65. Examples of such parameters include audio volume, video contrast, color saturation, frequency response or range, monaural versus stereo, depth perception, field of view, closeup versus wide-angle, presence or absence of VR or other supplemental sensory stimuli, scene duration, or any of various other parameters that tend to heighten or lessen sensory impact. In the case of an in vivo session in which scripts 152 are used to guide the patient 65 through the steps of planning and implementing graduated exposure to physical and/or sensory stimuli in the real environment, such as, by going to a location reminiscent of an event or that otherwise evokes distress, intensity might refer to distance from the location in question, or length of time present within the location in question, or whether the patient is alone or accompanied by a close person. It should be noted that such physical and/or sensory stimuli may also include objects, persons, sounds, smells, video or still photos, looking in the mirror, or even touch and taste stimuli.

As shown by block 552, as the stimulus 156 is being played back to the patient 65, the patient monitoring module 120 monitors the mental state of the patient 65 and generates a mental state metric.

Monitoring of the mental state of the patient 65 at this time may include self-reporting by way of the self-reporting module 122, monitoring of speech and/or facial affect by way of the audiovisual monitoring module 124, and monitoring of any of various biological or physiological phenomena by way of the physiologic module 126. Although block 552 is for convenience shown as a single block at a specific location in the flowchart of FIG. 5, monitoring of the patient 65 may actually take place over an extended period of time or at multiple points during the method of the flowchart of FIG. 5. For example, the patient 65 might be asked to indicate self-reported anxiety, stress, or distress level at regular time intervals, such as at every 15 seconds, during event playback. Furthermore, the mental state metric generated by the patient monitoring module 120 preferably reflects multiple measures of patient mental state as measured independently in different ways by the patient monitoring module 120. The patient monitoring module 120 stores the results of monitoring and/or the mental state metric in the form of a monitoring history 158 in the memory storage 150.

As shown by block 553, the mental state metric generated by the patient monitoring module 120 is evaluated to determine whether the mental state of the patient 65 is within safe limits. In the event that the mental state metric indicates that further playback of events might be unsafe for the patient 65, the session is ended. Conversely, if the mental state metric is within safe limits, processing proceeds to block 554.

As shown by block 554, a determination is made as to whether the amount of time set aside for the session has expired. For example, to avoid overtiring the patient 65, a predetermined maximum amount of time might be set in advance for the session. In the event that the time set aside for the session has expired, the session is ended. Conversely, if the time set aside for the session has not yet expired, processing proceeds to block 555.

As shown by block 555, a determination is made as to whether the patient 65 has habituated to the stimulus 156 that is being played back to the patient 65. That is, one goal of playback of events in accordance with the flowchart of FIG. 5 is to administer a treatment hierarchy designed to foster habituation in accordance with the goals of exposure therapy as intended by the therapist 55. What is meant by habituation (also known as "fear extinction") is that with repeated exposure the patient 65 becomes desensitized to the stimulus 156, such that the emotional response is appreciably reduced. Habituation can be determined by observing the value of the mental state metric that is measured during playback at block 552 of the flowchart in FIG. 5. For example, as a particular stimulus 156 is played back repeatedly to a patient 65, a therapist 55 might determine that a patient 65 had habituated when the mental state metric values stored in the form of a monitoring history 158 indicate a consistent trend indicative of steadily decreasing anxiety. As another example, the therapist 55 may determine that the patient 65 had habituated when the mental state metric value measured at step 552 of the flowchart in FIG. 5 indicates sufficient progress in desensitization relative to a baseline mental state metric value measured during recording of the stimulus 156 at block 532 of the flowchart at FIG. 4. In one embodiment, the hierarchy navigation module 140 may determine that the patient 65 has habituated to the stimulus 156 if the value of the mental state metric measured during playback of the stimulus 156 at block 552 of the flowchart of FIG. 5 is less than or equal to a predetermined fraction of the value of the baseline mental state metric measured during recording of the stimulus 156 at step 532 of the flowchart at FIG. 4.

In the event that it is determined at block 555 that the patient 65 has not yet habituated to the stimulus 156, processing proceeds to block 558. At block 558 of the exemplary flowchart in FIG. 5, in accordance with rules 154 stored in the memory storage 150, the intensity module 144 optionally adjusts playback intensity to what is expected to be a suitable level based on patient mental state and/or session history before commencing another loop through the flowchart of FIG. 5 from block 551. Conversely, if it is determined at block 555 that the patient 65 has habituated to the stimulus 156, processing proceeds to block 556.

As shown by block 556, a determination is made as to whether the patient 65 has habituated to the event as a whole. That is, events recounted by the patient 65 during recording of events in accordance with the flowchart of FIG. 4 are parsed into stimuli 156 by the parsing module 132, and these stimuli 156 are played back to the patient 65 by the hierarchy navigation module 140 during playback of events in accordance with the flowchart of FIG. 5. In one embodiment, the hierarchy navigation module 140 may determine that the patient 65 has habituated to the event as a whole when the patient 65 has habituated sufficiently to the stimuli 156 that make up that event. In another embodiment, the hierarchy navigation module 140 might shuffle or otherwise randomly select stimuli 156 for playback until all stimuli 156 making up the event consistently yield mental state metric values indicative of habituation. In yet another embodiment, the hierarchy navigation module 140 might determine that the patient 65 has habituated to the event when repeated playback of stimuli 156 determined to be relevant based on baseline mental state metric values consistently yields mental state metric values indicative of habituation.

In the event that it is determined at block 556 that the patient 65 has not yet habituated to the event as a whole, processing proceeds to block 557. As shown by block 557 of the exemplary flowchart in FIG. 5, in accordance with rules 154 stored in the memory storage 150, the sequence module 142 optionally selects a different stimulus 156 based on patient mental state and/or session history. Thereafter, as shown by block 558, the intensity module 144 optionally adjusts playback intensity to what is expected to be a suitable level based on patient mental state and/or session history, before commencing another loop through the flowchart of FIG. 5 from block 551.

Conversely, if it is determined at block 556 that the patient 65 has habituated to the event, processing for playback of the event is ended at block 569. If session time has not yet expired, the therapist 55 or the hierarchy navigation module 140 may select another event for playback to the patient 65, upon which playback of that event may be carried out after returning to block 551 of the flowchart of FIG. 5.

The foregoing is merely one exemplary embodiment intended to demonstrate various aspects of the present invention. A great many variations are possible, these variations being within the scope of the invention as set forth by the claims below.

For example, there is no particular limitation as to where the various functional blocks shown in FIGS. 1 and 2 are located. Any of the functional blocks shown, or subsets thereof, may be at the same or at different sites. For example, in one embodiment, patient-related data such as stimuli 156 and monitoring history 158, and therapist-related data such as scripts 152 and rules 154 governing treatment, may be stored on a database at a central server, and the patient communication module 110 may communicate with the patient 65 by way of mobile telephone, personal digital assistant (PDA), laptop computer, or other such portable or remote device.

Furthermore, processor(s) 12 and memory or memories 14 for implementing the psychiatric disorder treatment system 10 shown in FIG. 1 may be associated with computer(s) used by the patient 65 and/or the therapist 55. Moreover, any of various aspects of the psychiatric disorder treatment system 10 may alternatively or in addition be implemented in the form of digital electronic circuitry, computer hardware, firmware, software, or any combination thereof The psychiatric disorder treatment system 10 may be implemented as a computer program product. What is meant by a computer program product is a computer program that has been tangibly embodied in an information carrier, e.g., in a machine-readable storage device or in a propagated signal, for execution by, or to control the operation of, a communications processing apparatus, e.g., a processing device, a computer, or multiple computers. Such computer program may be written in any form of programming language, including compiled, assembled, or interpreted languages. Furthermore, such computer program may be deployed in any form, including as a stand-alone program or as a module, component, subroutine, or other unit suitable for use in a computing environment. Moreover, such computer program may be deployed for execution on one computer or on multiple computers at one site or distributed across multiple sites and interconnected by a communication network.

Moreover, notwithstanding that an extensive psychiatric disorder treatment system 10 and software 100 have been shown in FIGS. 1 and 2 and described with reference to one or more embodiments, there is no particular objection to employment of any subset of the system and/or functionalities to practice any of various aspects of the present invention. In general, any suitable computer system or suitable computer-implemented technique may be employed to practice embodiments of the invention. For example, various computer-implemented techniques may be employed for generating control signals to any of various stimuli generators that may be employed at the patient communication module 110, or for receiving feedback from any of various input devices that may be employed at the patient monitoring module 120. As another example, any portion of the software 100, e.g., any of various training techniques that may be employed at block 510 of the flowchart of FIG. 3, may be implemented by way of a computer network, such as a local area network (LAN), wide area network (WAN), or a global computer network such as the Internet. Furthermore, any portion of the software 100, e.g., any of various evaluative techniques that may be employed at the flowcharts of FIGS. 4 and 5 may be implemented in whole or in part in the form of downloadable software and/or data. Such downloadable software and/or data may, for example, reside on one or more servers on a network, and may be accessible by any client computer or terminal capable and authorized for such access (via, for example, a web browser). Once downloaded, such a client computer or terminal might then be employed to control any of various stimuli generators at the patient communication module 110, as well as to gather responses from any of various monitoring devices at the patient monitoring module 12, for example. To facilitate or expedite processing, such downloadable computer software and/or data might be downloaded once and reused over and over at the client computer or terminal. Alternatively, such downloadable computer software and/or data might be downloaded, e.g., via network connection, for each individual treatment session or as needed. In such case, all or any portion of the software 100 might be executed at the server(s), with program outputs being transmitted to the client computer or terminal for interfacing with the I/O devices 16. Alternatively, execution may take place locally at the client computer or terminal after downloading. In such an embodiment, by transmitting stimuli 156, monitoring history 158, or other such patient-related data to another computer on the network, this may make it easier for a therapist 55 at a remote location to monitor participation and progress of the patient 65, such as, in real time or at regular intervals. In some embodiments, the therapist 55 would not only be able to monitor participation and progress of the patient 65 but would also be able to modify treatment, e.g., by changing the rules 154 governing treatment so as to accommodate a specific patient 65 or circumstance.

Ability to implement remote treatment may be especially useful for in vivo treatment in which scripts 152 are used to prompt the patient 65 to enter an environment reminiscent of an event, or in which the patient feels unsafe, or to otherwise approach stimuli that elicit distress. For example, such scripts 152 or other such information necessary for in vivo treatment might be downloaded to a PDA, smart phone, palmtop device, personal music or video player, laptop or notebook computer, or other such portable or remote device in the possession of the patient 65 so as to permit the patient 65 to undergo in vivo exposure therapy treatment by coming in contact with an environment that is not necessarily close to the location of a server at which various portions of the software 100 may reside or at which the therapist 55 may be present. Such scripts 152 could then direct the patient 65 through the steps of planning and implementing graduated exposure to physical and/or sensory stimuli in the real environment in accordance with the goals of in vivo exposure therapy treatment as intended by the therapist 55.

Although recording of events in accordance with the flowchart of FIG. 4 has been described as taking place under the control of the hierarchy assembly module 130, and playback of events in accordance with the flowchart of FIG. 5 has been described as taking place under the control of the hierarchy navigation module 140, in some embodiments the hierarchy assembly module 130 and the hierarchy navigation module 140 may cooperate such that navigation functionality is available to the hierarchy assembly module 130 during hierarchy assembly and/or hierarchy assembly functionality is available to the hierarchy navigation module 140 during hierarchy navigation. For example, during recording of events in accordance with the flowchart of FIG. 4, it may be advantageous to employ hierarchy navigation functionality to navigate within the framework of a treatment hierarchy as it is in the progress of being assembled. Similarly, during playback of events in accordance with the flowchart of FIG. 5, it may be advantageous to employ hierarchy assembly functionality to further fill in and/or modify a treatment hierarchy as it is in the process of being navigated.

Although the present invention has been described in terms of an example in which hierarchy assembly takes place at the time of recording, in some embodiments hierarchy assembly may take place at the time of playback, or at any time or times between the time of recording and the time of playback. Furthermore, although the present invention has been described in terms of an example in which an event is divided or parsed into stimuli, in some embodiments the stimuli need not be literal fragments of the original event but may be derived or synthesized from all or part of the event. That is, although the present invention has been described in terms of an example in which adjustment of stimulus intensity is separate and distinct from parsing of the event into stimuli, in some embodiments the stimuli may be different synthesized or derived versions of varying intensity of a single event. For example, in one embodiment, such synthesized or derived versions of varying intensity of a single event might be employed for administration of a treatment hierarchy in which increasingly higher-intensity versions of the same scenario are employed as the patient successfully habituates to each successive version following as many repetitions as it takes for this to occur. Note that, where present, such synthesized or derived versions of varying intensity of a single event may be assembled in advance and stored as synthesized or derived stimuli 156 in the database 150, or such synthesized or derived versions may be created as needed during administration of treatment based on raw or literal event fragments as stimuli 156 in the database 150.

Note that although one or more embodiments described above may for convenience employ the singular or plural with reference to patient(s), therapist(s), computer(s), network(s), or any of the components or functional blocks shown in FIGS. 1 and 2, this is meant to be representative only, and should not be interpreted as a disclaimer of either the singular or plural.

As described above, embodiments of the present invention provide a device, system, and method for treatment of psychiatric disorders. Embodiments of the present invention as described above make it possible to effectively deliver exposure therapy, including imaginal and/or in vivo treatment, for PTSD or other anxiety disorders or stress-based problems in the context of a psychiatric disorder treatment system implemented by way of a local computer machine, the Internet, or a portable computing device. For example, embodiments of the present invention make it possible to guide a patient through a complete, multi-session course of treatment for PTSD, including psychoeducation, treatment rationale, coping self-statement, and imaginal and in vivo exposure.

Furthermore, while embodiments of the present invention permit administration of treatment in primary care or mental health specialty settings with intervention or direction by a therapist, embodiments of the present invention also permit self-administration, e.g., in a preclinical context, in which a patient accesses the system independently without the need for intervention from a therapist. Automation of aspects of exposure therapy in accordance with embodiments of the present invention may help reduce barriers to dissemination of exposure therapy, especially where patients would rather self-administer than see a therapist, or where patients have no objection to obtaining treatment from a therapist but there are a limited number of therapists available. By permitting access to exposure therapy outside the specialty mental health clinic, embodiments of the present invention address most of the barriers identified by Hoge et al at and facilitate widespread dissemination of exposure therapy for PTSD, for example. For reference, these barriers can be found in the following article: Hoge, C. W., Castro, C. A., Messer, S. C., McGurk, D., Cotting, D. I., & Koffman, R. L. (2004). Combat Duty in Iraq and Afghanistan, Mental Health Problems, and Barriers to Care. New England Journal of Medicine, 351(1), 13-22.

Besides making it possible for a patient to receive treatment with little or no intervention from a therapist, embodiments of the present invention may further improve efficiency by allowing a therapist to treat multiple patients at once, or by allowing patients to receive treatment at a location or multiple locations that are distant from therapists. For example, complete or partial automation in some embodiments of such tasks as hierarchy assembly and hierarchy navigation can greatly reduce the amount of time a therapist must spend with a patient, increase the number of patients who can be treated, and improve quality and consistency of the therapy that is delivered. For example, a fully self-help embodiment of the present invention makes it possible to provide treatment privately and without stigma.

Moreover, various computer-implemented features of embodiments of the invention as described above may provide one or more advantages as compared with conventional exposure therapy. For example, various types of multimedia content, such as, but not limited to, video, audio, animation, graphics, and text, may be employed. For example, such content may be advantageously employed during an introductory or educational session in which the patient is familiarized with the technique and equipment. Further, the program will enable clinical decisions to be guided by an array of parameters indicative of patients' mental state, including physiological and behavioral measures in addition to conventionally used self-reported ratings of distress, which have the potential to enhance the clinical utility of exposure therapy delivered by computer as compared to that delivered by therapists.

In some embodiments, ability of a patient to access the psychiatric disorder treatment system remotely, such as, by way of a network such as the Internet, may be facilitated by implementing the system in the context of a portable computing device. Such a portable computing device may take the form of a smart phone, palmtop device, personal music or video player, laptop or notebook computer, or portable gaming console. For example, implementation of the system in the context of such a portable computing device will permit portable or remote monitoring and guiding for in vivo treatment in which the patient is prompted to enter a location that is the scene of or that is reminiscent of the scene of a traumatic event. For example, palmtop versions of the system can provide a portable and easily disseminated means of delivering an effective PTSD treatment.

For example, in one embodiment, monitoring of the patient might be carried out by having the patient might wear an actigraph or actimetry sensor, this being a wristwatch-like device capable of being worn on the arm or leg for measuring motion. Such an actigraph would be useful for monitoring wake/sleep cycles or phases of sleep as indicative of patient mental state. This might be particularly helpful in a situation where the imaginal material employed is associated with nightmares experienced by the patient.

When the patient is not in the presence of the therapist, implementation of a patient communication module and a patient monitoring module make it possible for the therapist to communicate with and monitor the mental state of the patient. In some embodiments, the improved monitoring and real-time data input from the patient 65, such as, in the form of self-reported anxiety level, speech and facial analysis, and/or physiological data, may provide a better indication of the mental state of the patient than the therapist would have during a conventional therapy session. For example, because embodiments of the present invention may monitor speech, facial affect, and/or any of various biological or physiological parameters, alone or in combination with SUDS or other self-reported distress level, treatment decisions during administration of exposure therapy may be made more accurately and permit faster or better habitation than is the case conventionally. In particular, supplementing of self-reported distress level with other measures of patient mental state not as prone to problems of variability among patients or various reporting biases makes it possible in some embodiments for the system to provide superior evaluation of patient mental state. Moreover, because the system makes it possible to base treatment decisions on mental state metric values that integrate or otherwise reflect the mental state of the patient as measured in a plurality of ways, more accurate evaluation of patient mental state is permitted. In addition, portable monitoring of patient state used during in vivo exposure may be extended to collect data on stress responses in daily life as indices of clinical improvement that might be incorporated in clinical decision making, assessment of treatment outcome and to aid investigations into mediators treatment change.

Moreover, unlike conventional computer-implemented treatment systems employing content created based on the imagination of a computer programmer or based on a supposed generic narrative presumed to apply to the patient, because the exposure therapy that is administered in some embodiments of the present invention is created based on actual input from the patient, treatment in accordance with such embodiments can be expected to be more effective because it is specific to what the patient actually experienced.

Furthermore, some embodiments of the present invention may provide other benefits and advantages. Note, however, that the present invention is not intended to be limited to a device, system, or method that must satisfy one or more of any stated objects or features of the invention.

Modifications and substitutions by one of ordinary skill in the art are considered to be within the scope of the present invention, which is not to be limited except by the following claims. It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A computer-based system for treating a patient having a psychiatric disorder, the system comprising:
 a memory; and
 a processor configured to perform the steps of:
  recording a patient's recounting of an event that was experienced by the patient;
  parsing or dividing the recounted event into one or more stimuli for subsequent playback to the patient;
  generating a mental state metric for each of the one or more stimuli, wherein each mental state metric is indicative of a mental state of the patient at a time when an associated stimulus was being recounted; and
  causing a selected one of the stimuli to be played back to the patient one or more times,
  wherein a mental state of the patient is monitored as the selected one of the stimuli is played back one or more times, and
  wherein a different one of the stimuli is selected for subsequent play back to the patient based on the monitored mental state of the patient.

2. The computer-based system of claim 1, further comprising:
 a patient interface for playing back one or more of the stimuli, including providing or directing visual and audio exposure; and
 a sensor for monitoring the mental state of the patient, including sensing a level of patient anxiety or distress.

3. The computer-based system of claim 1, wherein the processor is further configured to perform the steps of:
 associating, with each of the stimuli, a first mental state metric value representative of the monitored mental state of the patient when the patient recounted the stimulus; and
 associating, with each of the stimuli, a second mental state metric value representative of the monitored mental state of the patient when the stimuli was played back to the patient.

4. The computer-based system of claim 3 wherein the processor is furthermore configured to perform the step of:
 varying a sequence of the stimuli to be played back to the patient in correspondence to the second mental state metric value until the second mental state metric value indicates habituation of the patient as compared with the first mental state metric value.

5. The computer-based system of claim 3 Wherein the processor is furthermore configured to perform the step of:
varying an intensity of at least one of the stimuli in correspondence to the second mental state metric value until the second mental state metric value indicates habituation of the patient as compared with the first mental state metric value.

6. The computer-based system of claim 3 wherein the processor is further configured to cause the system to provide a course of imaginal exposure therapy.

7. The computer-based system of claim 6 wherein the imaginal exposure therapy is implemented by playing back a recording in the voice or image of the patient.

8. The computer-based system of claim 3 adapted to provide a course of in vivo exposure therapy.

9. The computer-based system of claim 8 wherein the in vivo exposure therapy is implemented through use of a portable computing device that guides the patient to approach and be exposed to at least one of the stimuli.

10. The computer-based system of claim 3 wherein the first and second mental state metric values are based at least in part on. self-reported mental state information.

11. The computer-based system of claim 3 wherein the first and second mental state metric values are based at least in part on speech of the patient.

12. The computer-based system of claim 3 wherein the first and second mental state metric values are based at least in part on facial affect of the patient.

13. The computer-based system of claim 3 wherein-the first and second mental state metric values are based at least in part on at least one biological or physiological characteristic of the patient.

14. The computer-based system of claim 13 wherein the at least one biological or physiological characteristic includes a characteristic selected from the group consisting of breathing, heart rate, blood pressure, peripheral resistance, skin temperature, skin conductance, sweat gland activity, facial electromyographic response, peripheral muscle activity, restlessness, and shifting in chair.

15. The computer-based system of claim 3 wherein the processor is furthermore configured to perform the step of:
delivering coping statements to the patient in correspondence to the second mental state metric value.

16. The computer-based system of claim 1, wherein the processor is further configured to store in the memory a psychiatric disorder treatment data structure, the data structure comprising:
a plurality of the stimuli parsed from the event recounted by the patient; and
a historical record of the mental state metrics respectively associated with each of the stimuli;
wherein the mental state metrics respectively indicate monitored mental state of the patient during the recounting of the event by the patient and during at least one instance when at least one of the stimuli was used to administer exposure therapy to the patient.

17. The computer-based system of claim 3, wherein the processor is further configured to perform the steps of:
associating with each of the stimuli a mental state metric value representative of the monitored mental state of the patient when the patient experienced the stimulus; and
identifying one or more of the stimuli as being salient to treating the patient based on the mental state metrics associated with each of the stimuli.

18. The computer-based system of claim 3 further comprising:
hierarchy assembly means for creating a treatment hierarchy based on input from the patient; and
hierarchy navigation means for navigating within the treatment hierarchy in response to the mental. state of the patient.

19. A non-transitory computer-readable medium having stored thereon computer-executable instructions for configuring a processor to perform the steps of:
monitoring a mental state of a patient;
recording an event being recounted by the patient;
parsing the event into a plurality of stimuli;
controlling a sensory environment of the patient so as to administer exposure therapy to the patient based on at least one of the stimuli;
associating, with each of the stimuli on which the exposure therapy is based, a first mental state metric value representative of the monitored mental state of the patient when the patient recounted the stimulus; and
associating, with each of the stimuli on which the exposure therapy is based, a second mental state metric value representative of the monitored mental state of the patient when the exposure therapy based on the stimulus was administered to the patient.

20. A computer-readable medium according to claim 19 having further stored thereon computer-executable instructions for configuring a processor to perform the step of:
varying a sequence of the stimuli on which the exposure therapy is based in correspondence to the second mental state metric value until the second mental state metric value indicates habituation of the patient as compared with the first mental state metric value.

21. A computer-readable medium according to claim 19 having further stored thereon computer-executable instructions for configuring a processor to perform the step of:
varying an intensity of at least one of the stimuli on which the exposure therapy is based in correspondence to the second mental state metric value until the second mental state metric value indicates habituation of the patient as compared with the first mental state metric value.

22. A computer-readable medium according to claim 19 wherein the controlled sensory environment is an. imaginal environment implemented by playing back a recording of the voice or image of the patient.

* * * * *